United States Patent
Qian et al.

(10) Patent No.: US 10,874,403 B2
(45) Date of Patent: Dec. 29, 2020

(54) SEMI-AUTOMATIC MEDICAL CONTINUOUS-FIRING CLIP APPLIER HAVING BIOLOGICAL CLIP CARTRIDGE

(71) Applicant: JIANGSU HAIZE MEDICAL SCIENTIFIC DEVELOPMENT CO., LTD., Wuxi (CN)

(72) Inventors: Jianmin Qian, Wuxi (CN); Yun Sun, Wuxi (CN); Hailong Ju, Wuxi (CN)

(73) Assignees: JIANGSU HAIZE MEDICAL SCIENTIFIC, Jiangsu (CN); DEVELOPMENT CO., LTD., Jiangsu (CN)

(*) Notice: Subject to any disclaimer, the term of this patent is extended or adjusted under 35 U.S.C. 154(b) by 287 days.

(21) Appl. No.: 16/054,901

(22) Filed: Aug. 3, 2018

(65) Prior Publication Data
US 2019/0125351 A1 May 2, 2019

Related U.S. Application Data

(63) Continuation of application No. PCT/CN2016/098306, filed on Sep. 7, 2016.

(30) Foreign Application Priority Data

Jun. 20, 2016 (CN) .......................... 2016 1 0437045

(51) Int. Cl.
*A61B 17/128* (2006.01)
*A61B 17/122* (2006.01)
*A61B 17/29* (2006.01)

(52) U.S. Cl.
CPC ........ *A61B 17/1285* (2013.01); *A61B 17/122* (2013.01); *A61B 17/128* (2013.01);
(Continued)

(58) Field of Classification Search
CPC ... A61B 17/128; A61B 17/1285; A61B 17/29; A61B 17/2909; A61B 2017/2902;
(Continued)

(56) References Cited

U.S. PATENT DOCUMENTS

| 4,246,903 A | * | 1/1981 | Larkin | ................. | A61B 17/128 29/243.56 |
| 4,450,839 A | * | 5/1984 | Transue | ............... | A61B 17/128 606/143 |

(Continued)

FOREIGN PATENT DOCUMENTS

| CN | 101049251 A | 10/2007 |
| CN | 101617950 A | 1/2010 |

(Continued)

OTHER PUBLICATIONS

Jiangsu Haize Medical Scientific Development Co. Ltd., International Search Report and Written Opinion, PCT/CN2016/098306, dated Mar. 1, 2017, 17 pgs.
(Continued)

*Primary Examiner* — Ryan J. Severson
(74) *Attorney, Agent, or Firm* — Morgan, Lewis & Bockius LLP

(57) ABSTRACT

A semi-automatic medical continuous-firing clip applier includes a grip and a forceps rod, one end of the forceps rod is connected to the grip, and the other end of the forceps rod is connected to an upper jaw and a lower jaw; the upper jaw and the lower jaw are connected to a trigger, where the forceps rod is internally provided with a biological clip cartridge; the upper jaw and the lower jaw are provided with biological clip positioning grooves; the forceps rod is further internally provided with a transmission mechanism respectively in coordination with the biological clip cartridge and a biological clip propelling apparatus. The biological clip propelling apparatus is configured to drive a biological clip
(Continued)

in the biological clip cartridge to enter the positioning grooves in the upper and lower jaws, and then the trigger is tightly held to close the biological clip.

11 Claims, 6 Drawing Sheets

(52) U.S. Cl.
CPC ............... *A61B 2017/2923* (2013.01); *A61B 2017/2936* (2013.01)

(58) Field of Classification Search
CPC .... A61B 2017/2912; A61B 2017/2925; A61B 2017/2932
See application file for complete search history.

(56) References Cited

U.S. PATENT DOCUMENTS

| | | | | |
|---|---|---|---|---|
| 4,850,355 A * | 7/1989 | Brooks | ............... | A61B 17/128 606/143 |
| 5,199,566 A * | 4/1993 | Ortiz | ............... | A61B 17/1285 206/339 |
| RE35,525 E * | 6/1997 | Stefanchik | ......... | A61B 17/1285 606/142 |
| 6,423,079 B1 * | 7/2002 | Blake, III | .......... | A61B 17/1285 606/143 |
| 6,869,435 B2 * | 3/2005 | Blake, III | .......... | A61B 17/1285 606/143 |
| 7,081,121 B2 * | 7/2006 | Muramatsu | ........ | A61B 17/1227 606/139 |
| 7,419,495 B2 * | 9/2008 | Menn | ............... | A61B 17/128 227/175.4 |
| 7,520,882 B2 * | 4/2009 | Muramatsu | ........ | A61B 17/1227 606/139 |
| 7,621,926 B2 * | 11/2009 | Wixey | .................. | A61B 17/12 606/142 |
| 7,637,917 B2 * | 12/2009 | Whitfield | ............. | A61B 17/122 606/143 |
| 7,686,820 B2 * | 3/2010 | Huitema | ............... | A61B 17/10 606/142 |
| 8,236,012 B2 * | 8/2012 | Molitor | .............. | A61B 17/1285 606/143 |
| 8,267,944 B2 * | 9/2012 | Sorrentino | ............. | A61B 17/12 606/143 |
| 9,931,123 B2 * | 4/2018 | Blake, III | .......... | A61B 17/1285 |
| 10,098,641 B1 * | 10/2018 | Blake, III | .......... | A61B 17/1285 |
| 10,159,491 B2 * | 12/2018 | Gokharu | ......... | A61B 17/1222 |
| 10,368,876 B2 * | 8/2019 | Bhatnagar | .......... | A61B 17/1285 |
| 10,383,637 B2 * | 8/2019 | Castro | ................ | A61B 17/1285 |
| 2002/0133178 A1 * | 9/2002 | Muramatsu | ........ | A61B 17/1227 606/142 |
| 2003/0135224 A1 * | 7/2003 | Blake, III | .......... | A61B 17/1285 606/143 |
| 2006/0079911 A1 * | 4/2006 | Muramatsu | ........ | A61B 17/1227 606/139 |
| 2007/0049950 A1 * | 3/2007 | Theroux | ............ | A61B 17/1285 606/142 |
| 2011/0218554 A1 * | 9/2011 | Cheng | .................... | A61B 17/10 606/143 |
| 2016/0262764 A1 * | 9/2016 | Gokharu | ............ | A61B 17/1285 |
| 2017/0027576 A1 * | 2/2017 | Castro | ................ | A61B 17/1285 |
| 2018/0070948 A1 * | 3/2018 | Tan | .................... | A61B 17/1222 |
| 2019/0076150 A1 * | 3/2019 | Gokharu | ............ | A61B 17/1285 |
| 2019/0125351 A1 * | 5/2019 | Qian | ................ | A61B 17/1285 |
| 2019/0298377 A1 * | 10/2019 | Castro | ................ | A61B 17/1222 |

FOREIGN PATENT DOCUMENTS

| | | |
|---|---|---|
| CN | 204106108 U | 1/2015 |
| CN | 104490446 A | 4/2015 |
| CN | 104523316 A | 4/2015 |

OTHER PUBLICATIONS

Jiangsu Haize Medical Scientific Development Co. Ltd., International Preliminary Report on Patentability, PCT/CN2016/098306, dated Dec. 25, 2018, 6 pgs.

\* cited by examiner

SEMI-AUTOMATIC MEDICAL CONTINUOUS-FIRING CLIP APPLIER HAVING BIOLOGICAL CLIP CARTRIDGE

CROSS-REFERENCE TO RELATED APPLICATIONS

The application is a continuation application of PCT/CN2016/098306, entitled "SEMI-AUTOMATIC MEDICAL CONTINUOUS-FIRING CLIP APPLIER HAVING BIOLOGICAL CLIP CARTRIDGE" filed on Sep. 7, 2016, which claims priority to Chinese Patent Application No. 201610437045.4, entitled "SEMI-AUTOMATIC MEDICAL CONTINUOUS-FIRING CLIP APPLIER HAVING BIOLOGICAL CLIP CARTRIDGE" filed with the State Intellectual Property Office of the People's Republic of China on Jun. 20, 2016, the entirety of both of which is incorporated herein by reference.

TECHNICAL FIELD

The present disclosure relates to a minimally invasive medical instrument, in particular, to a reusable, misoperation-preventing medical biological clip continuous-firing clip applier, and specifically, to a medical continuous-firing clip applier that has a biological clip cartridge and that can semi-automatically and continuously perform feeding and firing and that is used for blood vessel occlusion in minimally invasive surgery.

BACKGROUND

During endoscopic surgery, when an organ or a tissue is severed, blood vessels need to be occluded, to prevent bleeding. Currently, two types of clip appliers are mainly used to resolve the problem of blood vessel occlusion. One is a reusable medical biological clip single-firing clip applier. Such a clip applier can effectively resolve the problem of blood vessel ligation in the endoscopic surgery. However, after closing each biological clip, a doctor needs to take the clip applier out of a human body, and give it to a nurse. The nurse puts a new hemostatic clip into forceps head jaws, and then gives the clip applier to the doctor to implement second clip application. Such operations are repeated, and two people are needed to complete clip application each time, consuming longer time. In addition, the clip applier repeatedly enters and exits the human body, increasing risks of infection and bleeding.

The other one is a medical titanium clip continuous-firing clip applier that can implement continuous firing, but is a disposable medical instrument and increases surgery costs. Moreover, a titanium clip for ligation is not elastic, is likely to conduct electricity, cannot be absorbed by the human body, and affects MRI imaging examination after the surgery.

The Chinese Patent 201510009673.8, "AUTOMATIC CONTINUOUS-FIRING BLOOD VESSEL PLASTIC CLIP APPLIER AND CLIP CARTRIDGE", provides a novel clip applier that is invented for overcoming disadvantages of the foregoing two types of clip appliers and that can perform clip application continuously, where a hemostatic clip used is a biological clip. However, the design of the novel clip applier has some disadvantages:

1. When being continuously fed, the biological clips are likely to fall off or deviate. The design of the patent is: A hemostatic clip in a hemostatic clip cartridge abuts against a spring mechanism disposed in a clip applier, the spring mechanism already stores energy before the hemostatic clip is fired, when a firing mechanism is enabled, the spring mechanism enters an energy releasing phase, and the hemostatic clip is pushed by the spring mechanism to enter a clip applying platform on a foremost end of the clip applier (clip feeding). After blood vessel occlusion is completed, under the action of the spring mechanism, a second hemostatic clip automatically enters the clip applying platform. The disadvantages of the design are: Under the action of energy released by the spring mechanism, the hemostatic clip automatically enters the clip applying platform, but in the energy releasing phase of the spring mechanism, there is not a corresponding control mechanism in the clip applier. This may result in that when a clip applying action of a current former hemostatic clip is performed, a next hemostatic clip already automatically pops out and enters the clip applying platform. That is, the next hemostatic clip may collide with the current hemostatic clip and fall off, affecting reliability and stability of an operation.

2. In the patent, a front end of the clip applier is provided by design with a fixed clip applying platform, and the platform is fixed in a clip applying process. Ligation of the blood vessels can only be implemented by using a flipping mechanism. Therefore, the clip applying action is a single joint action, and when the hemostatic clip is closed, there is a risk of an insufficient closing force.

Based on the above, it is needed to design a novel continuous-firing clip applier that implements continuous firing and closing of the hemostatic clips by repeatedly and manually performing feeding, so as to satisfy a clinical requirement and improve surgery safety and efficiency.

SUMMARY

Technical solutions of the present disclosure include the following:

A semi-automatic medical continuous-firing clip applier having a biological clip cartridge is provided, including a grip 1, a trigger 2, a biological clip propelling apparatus 3, a forceps rod 6, an upper jaw 7, and a lower jaw 8. One end of the forceps rod 6 is connected to the grip 1, and the other end of the forceps rod 6 is connected to the upper jaw 7 and the lower jaw 8. The upper jaw 7 and the lower jaw 8 are connected to the trigger 2 by using a connecting rod drive mechanism mounted in the forceps rod 6 and the grip 1. The forceps rod 6 is internally provided with a biological clip cartridge 9, and a plurality of biological clips 10 is mounted in the biological clip cartridge 9. The upper jaw 7 and the lower jaw 8 are provided with biological clip positioning grooves. The forceps rod 6 is further internally provided with a transmission mechanism respectively in coordination with the biological clip cartridge 9 and the biological clip propelling apparatus 3.

Each time when the biological clip propelling apparatus 3 is operated, a biological clip 10 that is closest to the upper jaw 7 and the lower jaw 8 and that is in the biological clip cartridge 9 is driven to enter the positioning grooves in the jaws, and then the trigger 2 is tightly held to close the biological clip 10. By means of repeating the foregoing two operations one more time, a next biological clip in the biological clip cartridge 9 enters the positioning grooves in the jaws and is closed. Continuous firing is implemented by means of repeated operations. If the grip 1 is provided with a safety lock 4, the semi-automatic medical continuous-firing clip applier having a biological clip cartridge is characterized in that: each time when the biological clip propelling apparatus 3 is operated, the apparatus is locked by the safety lock 4 and cannot return to an original state. An unlock button 401 on the safety lock 4 needs to be pressed before a next operation, and then the safety lock 4 can be unlocked, to return the biological clip propelling apparatus 3 to its original position.

A rotating wheel 5 apparatus is disposed between the grip 1 and the forceps rod 6, and when rotating, the rotating wheel 5 actuates the forceps rod 6, the upper jaw 7 and the lower jaw 8 mounted on the end of the forceps rod 6, and the biological clip cartridge 9 to synchronously rotate.

The biological clip cartridge 9 is internally provided with a slide rod and a spring mechanism, the slide rod is provided with a ratchet tooth, a cartridge wall is provided with a limiting structure, and the slide rod coordinates with the spring mechanism to control a stroke and stability of propelling the biological clip 10. Specifically, the biological clip cartridge 9 includes a cartridge cap 901, a cartridge base 902, a biological clip push head 903, a push member return spring 904, a reciprocating push member 905 and a cartridge cover 906.

After being fastened together, the cartridge base 902 and the cartridge cover 906 form a case, the biological blood vessel clips 10 are disposed on one end of the case, a last biological blood vessel clip 10, distal to an exit end, in the case abuts against one end of the biological clip push head 903, and the other end of the biological clip push head 903 is provided with a ratchet tooth that abuts against a propelling tooth on the reciprocating push member 905; a force applying end of the reciprocating push member 905 extends out of the case to abut against a push rod 11; and one end of the push member return spring 904 abuts against the reciprocating push member 905, and the other end abuts against a boss in the case.

A guide groove 908 that guides the reciprocating push member 905 and limits a stroke thereof is disposed on the cartridge base 902 or the cartridge cover 906, and a protruding block 909 disposed on the reciprocating push member 905 is inserted into the guide groove 908.

An inner side surface of the cartridge base 902 and/or the cartridge cover 906 is provided with a backstop structure 907 that enables the biological clip push head 903 to only move forward and not retract.

The backstop structure 907 is an obliquely protruding structure formed by a vertical plane and an oblique plane.

The beneficial effects of the present disclosure are:

By using a connecting rod technology, the present disclosure implements continuous, controllable, and stable blood vessel occlusion, satisfying a clinical requirement.

The present disclosure is provided with a safety lock mechanism to prevent a misoperation in a clip applying process.

When being used in endoscopic surgery, the present disclosure has advantages of safety and stability, and rapid and accurate clip application.

The continuous-firing clip application of the present disclosure improves clip application efficiency, reduces surgery time, and can maximally reduce bleeding, thereby reducing risks of surgery.

The apparatus of the present disclosure is reusable, and the biological clip cartridge is disposable, so that surgery costs are reduced.

DETAILED DESCRIPTION

The following further describes the present disclosure with reference to the accompanying drawings and embodiments.

The present disclosure is shown in FIG. 1 to FIG. 11.

Figure 1:
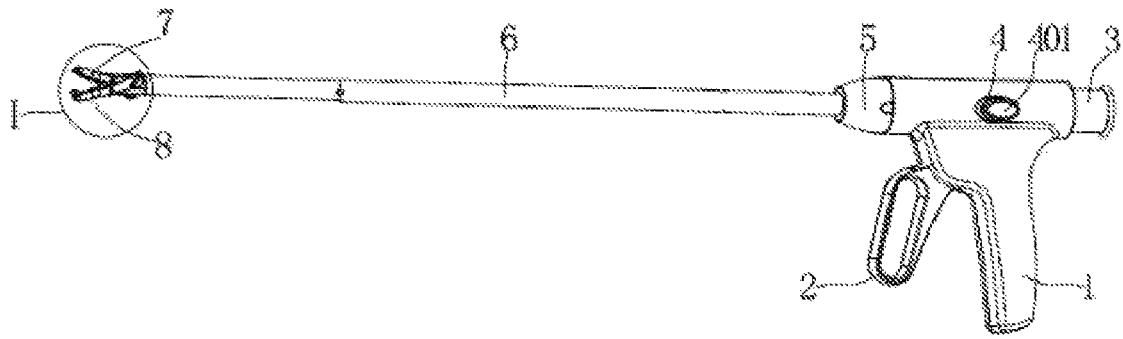
FIG. 1 is an axonometric view of the present disclosure.
Figure 2:
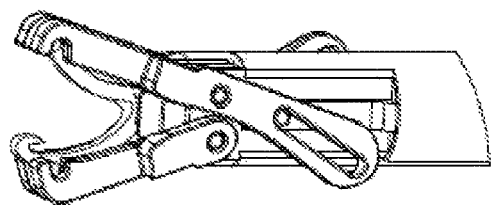
FIG. 2 is an enlarged view of a part I in FIG. 1.
Figure 3:
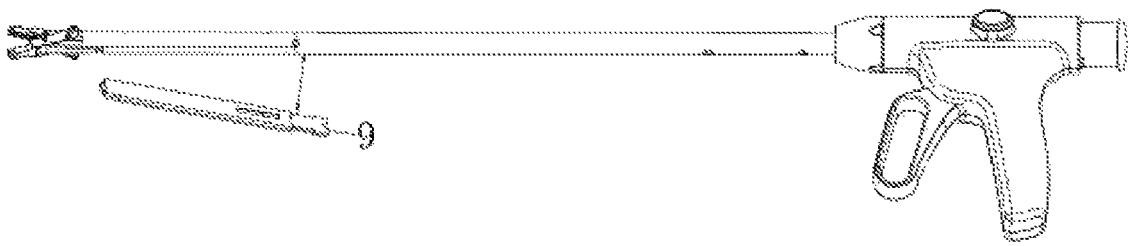
FIG. 3 is a schematic diagram of assembling and disassembling a biological clip cartridge according to the present disclosure.
Figure 4:
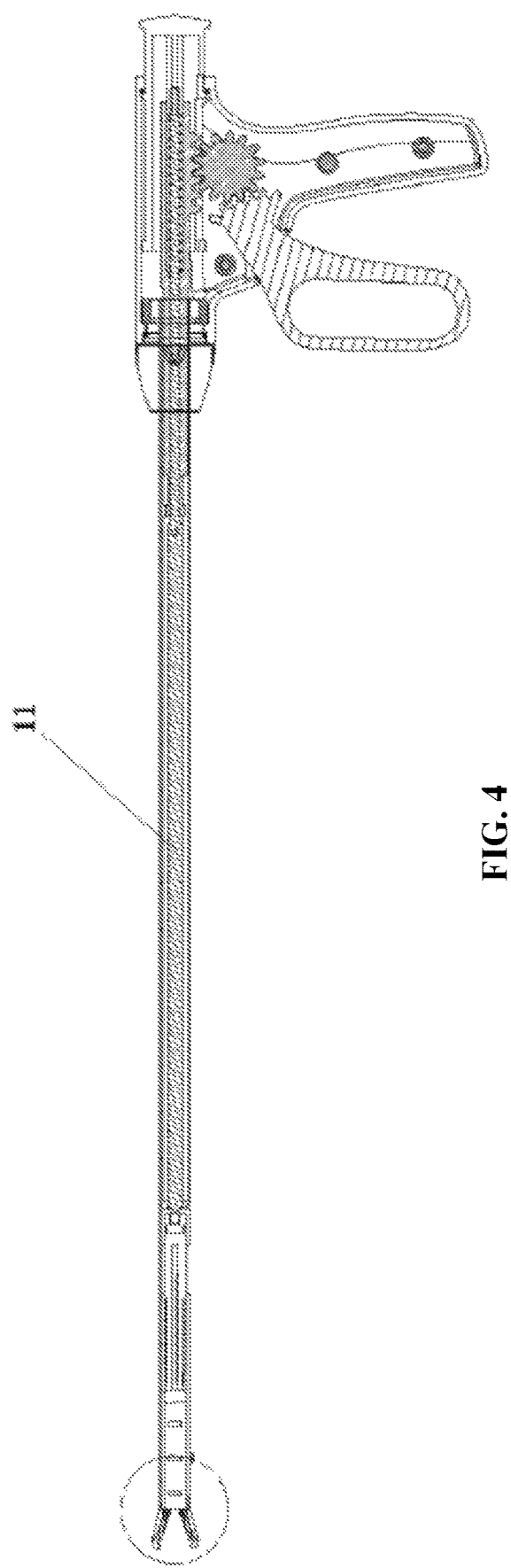
FIG. 4 is a front view and a front partial cross-sectional view of the present disclosure.
Figure 5:
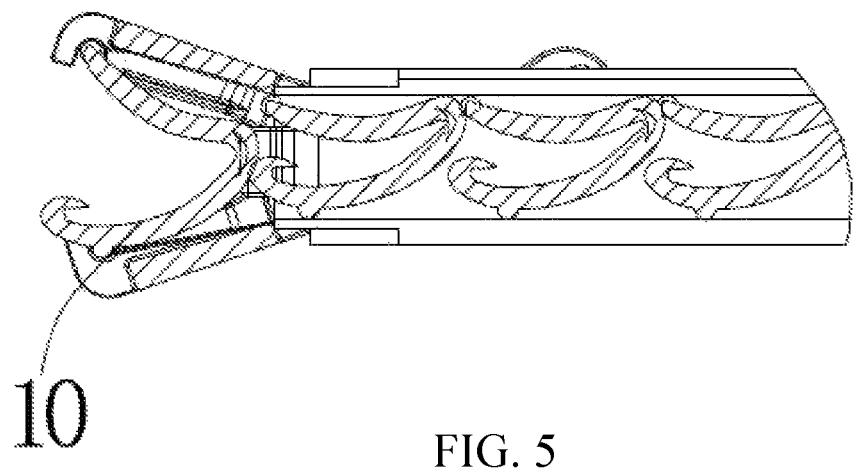
FIG. 5 is an enlarged view of a part II in FIG. 4.
Figure 6:
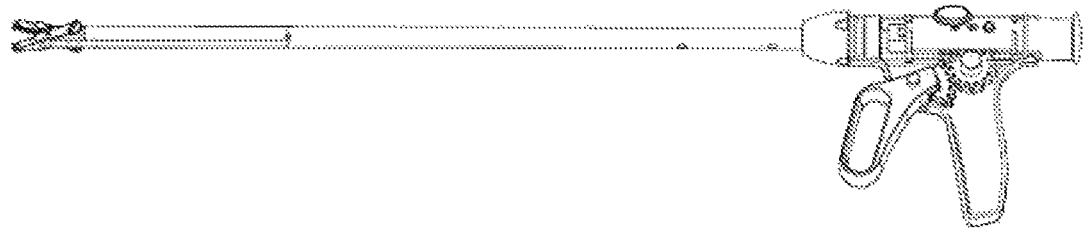
FIG. 6 is a schematic diagram of a grip.

A semi-automatic medical continuous-firing clip applier having a biological clip cartridge includes a grip 1, a trigger 2, a biological clip propelling apparatus 3, a forceps rod 6, an upper jaw 7, and a lower jaw 8. One end of the forceps rod 6 is connected to the grip 1, and the other end of the forceps rod 6 is connected to the upper jaw 7 and the lower jaw 8 (as shown in FIG. 1). The upper jaw 7 and the lower jaw 8 are connected to the trigger 2 by using a connecting rod drive mechanism mounted in the forceps rod 6 and the grip 1 (as shown in FIG. 6). The forceps rod 6 is internally provided with a biological clip cartridge 9 (as shown in FIG. 3), a plurality of biological clips 10 is mounted in the biological clip cartridge 9 (as shown in FIG. 4 and FIG. 5), and the biological clip cartridge 9 is internally provided with a slide rod and a spring mechanism, the slide rod is provided with a ratchet tooth, a cartridge wall is provided with a limiting structure, and the slide rod coordinates with the spring mechanism to control a stroke and stability of propelling the biological clip 10. The upper jaw 7 and the lower jaw 8 are provided with biological clip positioning grooves (as shown in FIG. 2 and FIG. 5). The forceps rod 6 is further internally provided with a transmission mechanism respectively in coordination with the biological clip cartridge 9 and the biological clip propelling apparatus 3.

Each time when the biological clip propelling apparatus 3 is operated, a biological clip 10 that is closest to the upper jaw 7 and the lower jaw 8 and that is in the biological clip cartridge 9 is driven to enter the positioning grooves in the jaws, and then the trigger 2 is tightly held to close the biological clip 10. By means of repeating the foregoing two operations one more time, a next biological clip in the biological clip cartridge 9 enters the positioning grooves in the jaws and is closed. Continuous firing is implemented by means of repeated operations. If the grip 1 is provided with a safety lock 4 (as shown in FIG. 1), each time when the biological clip propelling apparatus 3 is operated, the apparatus is locked by the safety lock 4 and cannot return to an original state. An unlock button 401 on the safety lock 4 needs to be pressed before a next operation, and then the safety lock 4 can be unlocked, to return the biological clip propelling apparatus 3 to its original position. A rotating wheel 5 apparatus is disposed between the grip 1 and the forceps rod 6 (as shown in FIG. 1), and when rotating, the rotating wheel 5 actuates the forceps rod 6, the upper jaw 7 and the lower jaw 8 mounted on the end of the forceps rod 6, and the biological clip cartridge 9 to synchronously rotate, so as to accurately and rapidly find a blood vessel occlusion position.

Figure 11:
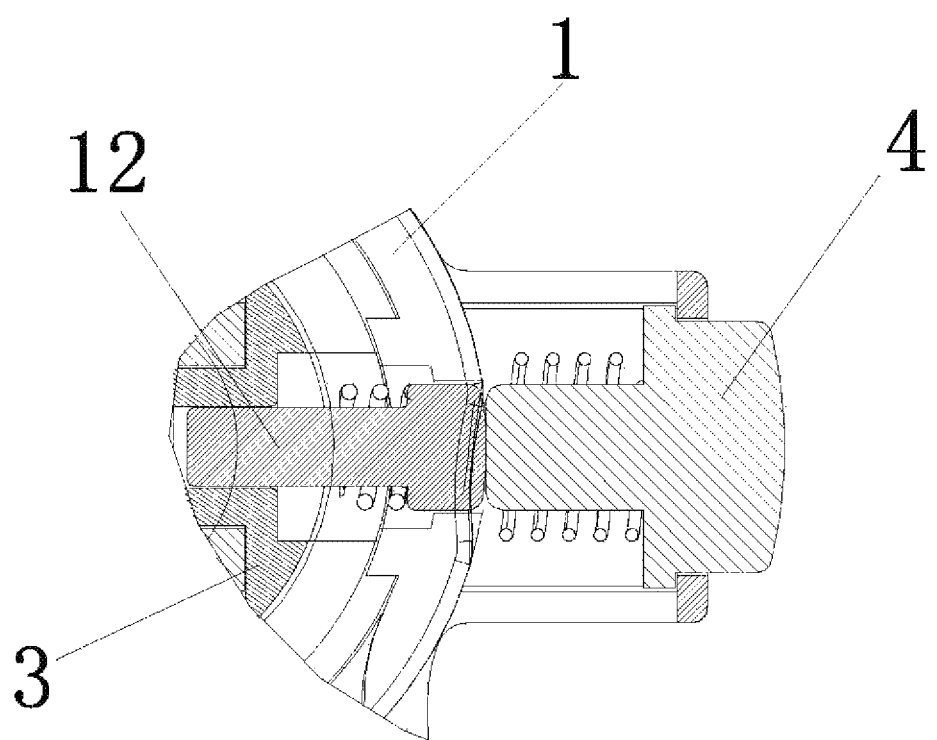
FIG. 11 is a schematic structural diagram of a safety lock according to an embodiment of the present disclosure.

During a specific implementation, the safety lock 4 may be designed according to requirements of the present disclosure, or be achieved by using a structure shown in FIG. 11. In FIG. 11, a pin 12 is mounted on the biological clip propelling apparatus 3, and when the biological clip propelling apparatus 3 is pressed into the grip, the pin 12 moves with the biological clip propelling apparatus 3. When moving to a hole position on the grip, under an action of an elastic force, the pin 12 extends into a pin hole that is inserted into the grip, to lock the biological clip propelling apparatus 3, so that the biological clip propelling apparatus 3 cannot move. After the unlock button 401 is pressed, the unlock button 401 forces the pin 12 to withdraw from the pin hole, and the biological clip propelling apparatus 3 returns to an original state under an action of an elastic force. When the unlock button 401 is released, the unlock button 401 departs from the pin hole in the grip and returns to an original state.

Figure 7:
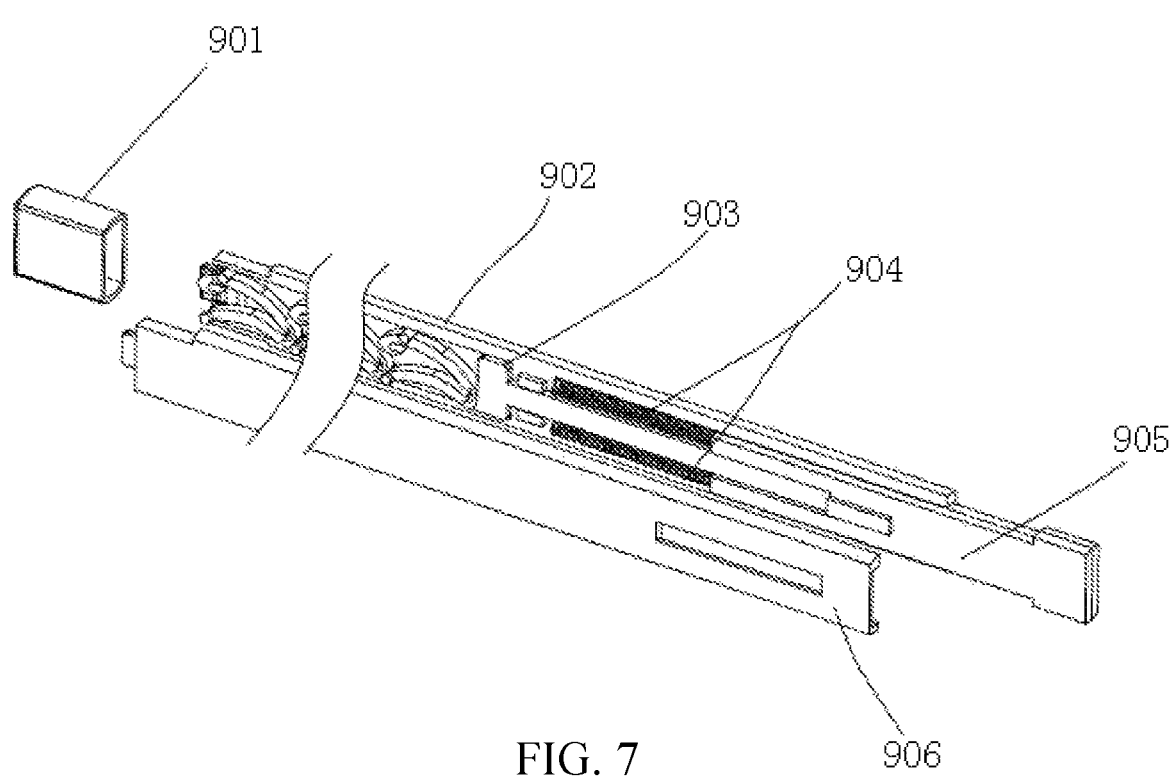
FIG. 7 is a schematic three-dimensional exploded structural diagram of a biological clip cartridge according to the present disclosure.
Figure 8:
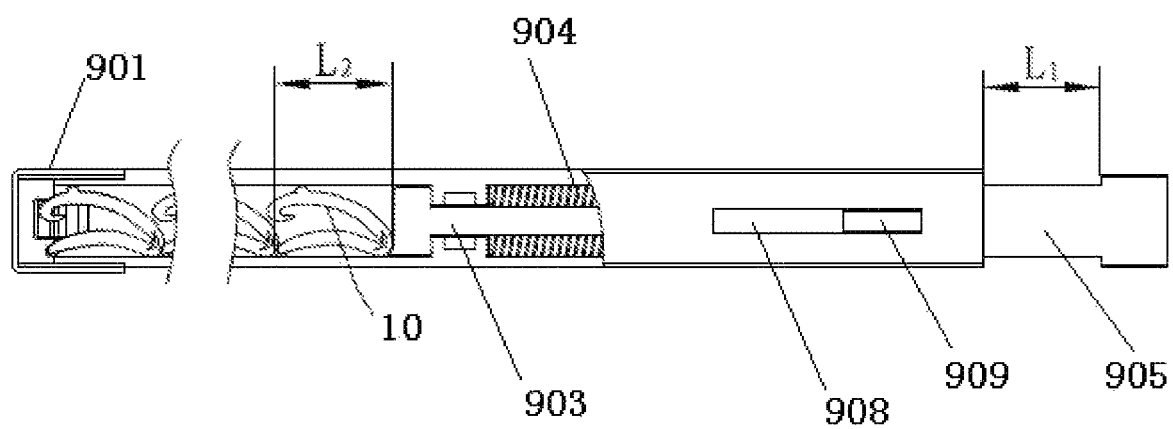
FIG. 8 is a schematic front structural diagram of FIG. 7.

During a specific implementation, the biological clip cartridge 9 of the present disclosure may be designed and manufactured according to the technical concept of the present disclosure, or be achieved with reference to content shown in FIG. 7 to FIG. 10. In FIG. 7, the biological clip cartridge 9 of the present disclosure includes a cartridge cap 901, a cartridge base 902, a biological clip push head 903, a push member return spring 904, a reciprocating push member 905 and a cartridge cover 906.

Figure 9:
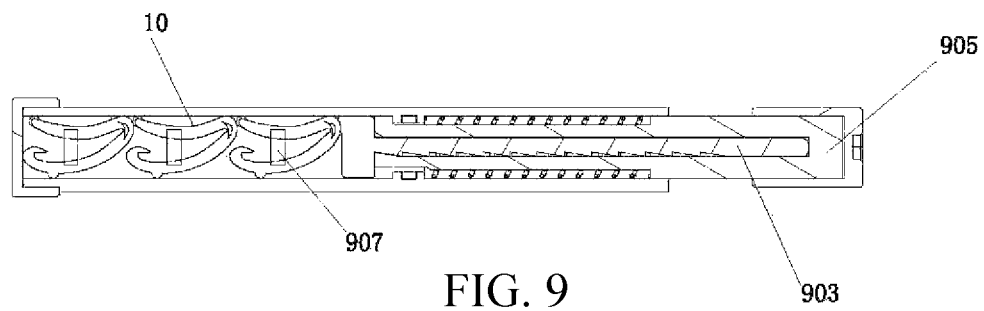
FIG. 9 is a schematic front sectional structural diagram of FIG. 8.

After being fastened together, the cartridge base 902 and the cartridge cover 906 form a case, the biological blood vessel clips 10 are disposed on one end of the case, a last biological blood vessel clip 10, distal to an exit end, in the case abuts against one end of the biological clip push head 903, and the other end of the biological clip push head 903 is provided with a ratchet tooth that abuts against a propelling tooth on the reciprocating push member 905, as shown in FIG. 9; a force applying end of the reciprocating push member 905 extends out of the case to abut against a push rod 11; and one end of the push member return spring 904 abuts against the reciprocating push member 905, and the other end abuts against a boss in the case.

Figure 10:
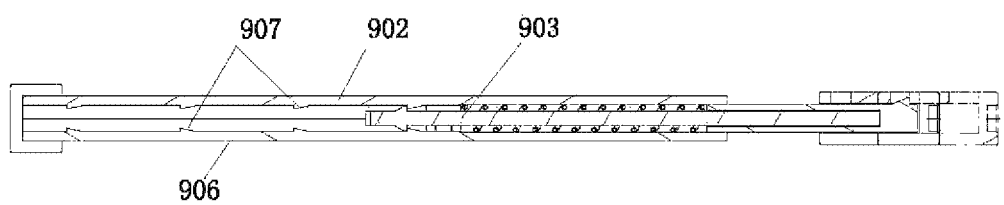
FIG. 10 is a schematic horizontal sectional structural diagram of FIG. 8.

A guide groove 908 that guides the reciprocating push member 905 and limits a stroke thereof is disposed on the cartridge base 902 or the cartridge cover 906, and a protruding block 909 disposed on the reciprocating push member 905 is inserted into the guide groove 908. An inner side surface of the cartridge base 902 and/or the cartridge cover 906 is provided with a backstop structure 907 that enables the biological clip push head 903 to only move forward and not retract, and the backstop structure 907 is an obliquely protruding structure formed by a vertical plane and an oblique plane, as shown in FIG. 10.

The reciprocating push member 905 moves forward by a distance L1 under an action of an external force, and the distance enables the biological blood vessel clip 10 to be pushed out by the biological clip push head 903 by a distance L2, to enable the biological blood vessel clip 10 to depart from the cartridge base 902. The biological blood vessel clip 10 is fully unfolded into a natural uncompressed state under the elasticity of its material, and the biological clip push head 903 is synchronously propelled by the distance L1 under an action of the reciprocating push member 905.

A method of using the present disclosure is:

A doctor takes the semi-automatic medical continuous-firing clip applier having a biological clip cartridge from a hand of a nurse, and makes it pass through a trocar and enter a human body. The upper jaw 7 and the lower jaw 8 are naturally opened to an angle needed for clip application, and then the biological clip propelling apparatus 3 is pressed to feed the biological clip 10 into the positioning grooves in the jaws. If the grip 1 is additionally provided with the safety lock 4, the apparatus is temporarily locked by the safety lock 4 and cannot return to the original state.

To fire a second biological clip, the doctor presses the unlock button 401 once to unlock the safety lock 4 and enable the biological clip propelling apparatus 3 to return to its original position, so as to operate the apparatus to fire. In this way, it is prevented that when the doctor performs clip application, a current biological clip is pushed into the human body because the doctor feeds next two biological clips before the current biological clip occludes the blood vessel.

After feeding the biological clip 10 into the positioning grooves in the jaws, the doctor rotates the rotating wheel 5 according to a position at which the blood vessel needs to be occluded, adjusts an angle to point at the position, tightly holds the trigger 2, closes the clip to complete blood vessel occlusion, and releases the grip 1 to enable the biological clip 10 to depart from the jaws and remain on the blood vessel.

When the doctor occludes the blood vessel by using a second biological clip, the foregoing clip feeding and blood vessel occlusion actions are repeated. Details are not described herein again.

In addition, it should be noted that the embodiments, names and shapes of components, and the like described in the present disclosure may be different. Any equivalent and simply modified design and manufacture made according to the concepts, principles, features, or like of the present disclosure fall within the protection scope of the present disclosure patent.

Parts not described in the present disclosure are all the same as the prior art or may be achieved by using the prior art.

What is claimed is:

1. A semi-automatic medical continuous-firing clip applier, comprising:
    a grip and a forceps rod, wherein one end of the forceps rod is connected to the grip, and the other end of the forceps rod is connected to an upper jaw and a lower jaw;
    the upper jaw and the lower jaw are connected to a trigger by using a connecting rod drive mechanism mounted in the forceps rod and the grip, wherein the forceps rod is internally provided with a biological clip cartridge;
    the upper jaw and the lower jaw are provided with biological clip positioning grooves; and
    the forceps rod is further internally provided with a transmission mechanism respectively in coordination with the biological clip cartridge and a biological clip propelling apparatus,
    wherein the biological clip cartridge comprises a cartridge cap, a cartridge base, a biological clip push head, a push member return spring, a reciprocating push member and a cartridge cover, the cartridge base and the cartridge cover form a case after being fastened together.

2. The semi-automatic medical continuous-firing clip applier according to claim 1, wherein a plurality of biological clips is mounted in the biological clip cartridge.

3. The semi-automatic medical continuous-firing clip applier according to claim 1, wherein the biological clip propelling apparatus is configured to drive a biological clip in the biological clip cartridge to enter the positioning grooves in the upper and lower jaws, and then the trigger is tightly held to close the biological clip.

4. The semi-automatic medical continuous-firing clip applier according to claim 3, wherein a next biological clip in the biological clip cartridge is configured to enter the positioning grooves in the upper and lower jaws and is closed by means of repeating the foregoing two operations one more time.

5. The semi-automatic medical continuous-firing clip applier according to claim 1, wherein the grip is provided with a safety lock for preventing the biological clip propelling apparatus from returning to an original position after one operation and for allowing the biological clip propelling apparatus to return the original position after pressing an unlock button on the safety lock before a next operation.

6. The semi-automatic medical continuous-firing clip applier according to claim 1, wherein a rotating wheel apparatus is disposed between the grip and the forceps rod, and the rotating wheel is configured to actuate the forceps rod, the upper jaw and the lower jaw mounted on the end of the forceps rod, and the biological clip cartridge to synchronously rotate after being rotated.

7. The semi-automatic medical continuous-firing clip applier according to claim 1, wherein a plurality of biological clips are disposed on the case, a last one of the plurality of biological clips, distal to an exit end, in the case abuts against one end of the biological clip push head, and the other end of the biological clip push head is provided with a ratchet tooth that abuts against a propelling tooth on the reciprocating push member; a force applying end of the reciprocating push member extends out of the case to abut against a push rod; and one end of the push member return spring abuts against the reciprocating push member, and the other end abuts against a boss in the case.

8. The semi-automatic medical continuous-firing clip applier according to claim 1, wherein a guide groove that guides the reciprocating push member and limits a stroke thereof is disposed on the cartridge base or the cartridge cover, and a protruding block disposed on the reciprocating push member is inserted into the guide groove.

9. The semi-automatic medical continuous-firing clip applier according to claim 1, wherein an inner side surface of the cartridge base and/or the cartridge cover is provided with a backstop structure that enables the biological clip push head to only move forward and not retract.

10. The semi-automatic medical continuous-firing clip applier according to claim 9, wherein the backstop structure is an obliquely protruding structure formed by a vertical plane and an oblique plane.

11. The semi-automatic medical continuous-firing clip applier according to claim 1, wherein the biological clip cartridge can be mounted or removed through a side hole of the forceps rod or an end hole of the forceps rod.

* * * * *